United States Patent [19]

Razavi

[11] Patent Number: 5,589,556

[45] Date of Patent: *Dec. 31, 1996

[54] PROCESS AND CATALYST FOR PRODUCING CRYSTALLINE POLYOLEFINS

[75] Inventor: Abbas Razavi, Pâturage, Belgium

[73] Assignee: Fina Technology, Inc., Dallas, Tex.

[ * ] Notice: The term of this patent shall not extend beyond the expiration date of Pat. No. 5,243,002.

[21] Appl. No.: 184,533

[22] Filed: Jan. 21, 1994

Related U.S. Application Data

[60] Division of Ser. No. 925,950, Aug. 5, 1992, Pat. No. 5,304,523, which is a continuation-in-part of Ser. No. 419,157, Oct. 10, 1989, Pat. No. 5,162,278, which is a continuation-in-part of Ser. No. 220,007, Jul. 15, 1988, Pat. No. 4,892,851.

[51] Int. Cl.$^6$ ................................ C07C 2/08; C08F 4/64
[52] U.S. Cl. ..................... 526/170; 526/160; 526/127; 526/133; 526/134; 585/524; 502/152
[58] Field of Search .................... 526/170, 168, 526/129, 133, 134, 114, 116, 127

[56] References Cited

U.S. PATENT DOCUMENTS

| | | | |
|---|---|---|---|
| 5,155,080 | 10/1992 | Elder et al. | 502/152 |
| 5,223,467 | 6/1993 | Razavi | 502/152 |
| 5,223,468 | 6/1993 | Razavi | 502/152 |
| 5,225,500 | 7/1993 | Elder et al. | 526/127 |
| 5,243,002 | 9/1993 | Razavi | 526/170 |
| 5,278,265 | 1/1994 | Razavi | 526/170 |
| 5,292,838 | 3/1994 | Razavi | 526/160 |
| 5,334,677 | 8/1994 | Razavi et al. | 526/114 |

*Primary Examiner*—Asok Pal
*Attorney, Agent, or Firm*—Jim D. Wheelington; M. Norwood Cheairs

[57] ABSTRACT

Catalyst and process for the stereospecific propagation of a polymer chain derived from an ethylenically unsaturated monomer which contains 3 or more carbon atoms or is substituted vinyl compound. The catalysts comprise stereorigid metallocenes in which a structural bridge is not required for stereorigidity. The ring structures of the metallocene catalyst are substituted cyclopentadienyl rings. The substituent groups on the cyclopentadienyl rings impart stereorigidity to the catalyst by virtue of a sterically hindered relationship between the rings sufficient to prevent rotation of the rings. The catalyst is contacted with a $C_3$ + alpha olefin or other ethylenically unsaturated compound in a polymerization reaction zone and maintained in contact with the catalyst in the reaction zone under polymerization conditions to produce a stereospecific polymer.

20 Claims, 6 Drawing Sheets

PROCESS AND CATALYST FOR PRODUCING CRYSTALLINE POLYOLEFINS

This is a Divisional application of application Ser. No. 07/925,950 filed on Aug. 5, 1992, now U.S. Pat. No. 5,304,523 which is a continuation-in-part of application Ser. No. 07/419,157 filed Oct. 10, 1989 now U.S. Pat.No. 5,162,278, which is a continuation-in-part of application Ser. No. 07/220,007 filed Jul. 15, 1988 which issued as U.S. Pat. No. 4,892,851 on Jan. 9, 1990.

FIELD OF INVENTION

This invention relates to catalyst and processes for the production of crystalline polymers front ethylenically unsaturated compounds and more particularly to the production of a crystalline polyolefin by polymerization of propylene or higher alpha olefin with a stereorigid neutral or cationic metallocene catalyst having similar or dissimilar cyclopentadienyl rings without bridging components between the cyclopentadienyl rings.

BACKGROUND OF THE INVENTION

Stereospecific propagation may be applied in the polymerization of ethylenically unsaturated monomers such as $C_3+$ alpha-olefins, 1-dienes such as 1,3-butadiene and additional or substituted vinyl compounds such as vinyl aromatics, e.g., styrene or vinyl chloride, vinyl ethers such as alkyl vinyl ethers, e.g., isobutyl vinyl ether, or even aryl vinyl ethers. Stereospecific polymer propagation is probably of most significance in the production of polypropylene of isotactic or syndiotactic structure.

Syndiotactic polymers have a unique stereochemical structure in which monomeric units having enantiomorphic configuration of the asymmetrical carbon atoms follow each other alternately and regularly in the main polymer chain. Syndiotactic polypropylene was first disclosed by Natta et al. in U.S. Pat. No. 3,258,455. As disclosed in this patent, syndiotactic polypropylene can be produced by using a catalyst prepared from titanium trichloride and diethyl aluminum monochloride. A later patent to Natta et al., U.S. Pat. No. 3,305,538, discloses the use of vanadium triacetylacetonate or halogenated vanadium compounds in combination with organic aluminum compounds for producing syndiotactic polypropylene. U.S. Pat. No. 3,364,190 to Emrick discloses the use of a catalyst system composed of finely divided titanium or vanadium trichloride, aluminum chloride, a trialkyl aluminum and a phosphorus-containing Lewis base in the production of syndiotactic polypropylene. As disclosed in these patent references and as known in the art, the structure and properties of syndiotactic polypropylene differ significantly from those of isotactic polypropylene. Syndiotactic polymers are those in which long sequences of monomer units have an alternating relative configuration of the tertiary carbon atoms. Using the Fischer projection formula, the structure of a syndiotactic polymer is designated as:

The methyl groups attached to the tertiary carbon atoms of successive monomeric units in the chain lie on alternate sides of the plane of the polymer. In NMR nomenclature, this pentad is described as . . . rrrr . . . in which each "r" represents a "racemic" dyad, i.e., successive methyl groups on alternate sides of the plane. The percentage of r dyads in the chain determines the degree of syndiotacticity of the polymer.

The isotactic structure is typically described as having long sequences of monomer units with the same relative configuration of the tertiary carbon atoms. Using the Fischer projection formula, the stereochemical sequence of isotactic polypropylene is described as follows:

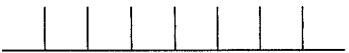

The methyl groups attached to the tertiary carbon atoms of successive monomeric units on the same side of a hypothetical plane through the main chain of the polymer, e.g., the methyl groups are all above or below the plane.

Another way of describing the structure is through the use of NMR. Bovey's NMR nomenclature for an isotactic pentad is . . . mmmm . . . with each m representing "meso" dyad or successive methyl groups on the same side in the plane. As known in the art, any deviation or inversion in the structure of the chain lowers the degree of isotacticity and crystallinity of the polymer.

Crystalline polymers, like isotactic and syndiotactic polymers, are insoluble in xylene. This crystallinity distinguishes both syndiotactic and isotactic polymers from an atactic polymer that is soluble in xylene. An atactic polymer exhibits no regular order of repeating unit configurations in the polymer chain and forms essentially a waxy product.

While it is possible for a catalyst to produce all three types of polymers, it is desirable for a catalyst to produce predominantly isotactic or syndiotactic polymer with very little atactic polymer. Catalyst that produce isotactic polyolefins are disclosed in European Patent Application No. 87870132.5 published as Publication No. 0 284 708 on Oct. 5, 1988; European Patent Application No. 878701 31.7 published as Publication No. 0 284 707 on Oct. 5, 1988 and European Patent Application No. 87870133.3 published as Publication No. 0 310 734 on Apr. 12, 1989. These applications disclose chiral, stereorigid metallocene catalysts that polymerize olefins to form isotactic polymers and are especially useful in the polymerization of a highly isotactic polypropylene.

Catalyst that produce syndiotactic polypropylene or other syndiotactic polyolefins are disclosed in the U.S. Pat. No. 4,892,851. These catalysts are bridged stereorigid metallocene catalysts. The catalysts have a structural bridge extending between dissimilar cyclopentadienyl groups and may be characterized by the formula:

$$R''(CpR_n)(CpR'_m)MeQ_k \qquad (1)$$

In formula (1), Cp represents a cyclopentadienyl or substituted cyclopentadienyl ring; and R and R' represent hydrocarbyl radicals having 1–20 carbon atoms. R" is a structural bridge between the rings imparting stereorigidity to the catalyst; Me represents a transition metal and Q a hydrocarbyl radial or halogen. $R'_m$ is selected so that $(CpR'_m)$ is a sterically different substituted cyclopentadienyl ring than $(CpR_n)$; n varies from 0 to 4 (0 designating no hydrocarbyl groups, i.e. an unsubstituted cyclopentadienyl ring) and m varies from 1–4, and k is from 0–3. The sterically different cyclopentadienyl rings produces a predominantly syndiotactic polymer rather than an isotactic polymer.

Metallocene catalysts of yet another type are cationic catalyst as disclosed in European Publication Nos. 277,003 and 277,004. As disclosed in these applications, a bis(cyclopentadienyl) zirconium, titanium or hafnium compound is reacted with a second compound comprising a cation capable of donating a proton or an ion exchange compound comprising a cation which will irreversible react with a ligand on the first compound, and a bulky, stable anion. The catalysts described in the European Publication Nos. 277,003 and 277,004 are disclosed as especially useful in the polymerization of ethylene and more generally in the polymerization of alpha olefins, diolefins and/or an acetylenically unsaturated compounds containing from 2–18 carbon atoms. Principally disclosed in the European Patent Application publications is the polymerization of ethylene or the copolymerization of ethylene with propylene or 1-butene or with propylene and 1-butene or 1,4 hexadiene. Stereospecificity, or lack thereof, of the polymers as disclosed in the European Patent Application publications is not generally discussed, although in Publication No. 277,004, examples are given of producing atactic polypropylene and in one instance (Example 39) isotactic polypropylene.

SUMMARY OF THE INVENTION

In accordance with the present invention, there are provided catalysts and processes for the stereospecific propagation of a polymer chain derived from an ethylenically unsaturated monomer which contains 3 or more carbon atoms or is a substituted vinyl compound. Catalysts in accordance with the present invention comprise stereorigid metallocenes in which a structural bridge of the type employed in the metallocene catalyst disclosed in U.S. Pat. No. 4,892,851 is not required for stereorigidity. The ring structures of the metallocene catalyst of the present invention are substituted cyclopentadienyl rings which include but are not limited to indenyl and fluorenyl. However, in the present invention the substituent groups on the cyclopentadienyl rings impart stereorigidity to the catalyst. In one aspect of the invention, the substituent groups on the cyclopentadienyl rings provide a sterically hindered relationship between the rings sufficient to prevent rotation of the rings and impart the stereorigidity to the catalyst. The metallocene catalysts have ring structures joined to a coordinating transition metal atom. The ring structures are both substituted cyclopentadienyl groups. Both of said cyclopentadienyl groups are in a stereorigid relationship relative to the coordinating transition metal atom to prevent rotation of said rings.

Crystalline polypropylene or other polymers resulting from the polymerization of $C_3+$ alpha olefins or vinyl compounds may be produced in accordance with the method of the present invention. Stereospecific propagation of the polymer chain is carried out in the presence of a stereorigid metallocene catalyst which incorporates substituted cyclopentadienyl rings, both of which are in a stereorigid relationship as described above relative to the coordinating metal atom of the metallocene complex. The catalyst is contacted with a $C_3+$ alpha olefin or other ethylenically unsaturated compound in a polymerization reaction zone and maintained in contact with the catalyst in the reaction zone under polymerization conditions to produce a syndiotactic polymer. The preferred application of the invention is in the production of isotactic polypropylene.

Catalysts in which the aforementioned stereorigid relationship between the cyclopentadienyl rings is established in accordance with the present invention may be characterized by formula (2) as follows.

Wherein:

Cp is a cyclopentadienyl or a substituted cyclopentadienyl ring;

each S is the same or different and is a hydrocarbyl radical having from 1–20 carbon atoms;

each S' is the same or different and is a hydrocarbyl radical having from 1–20 carbon atoms; and $CpS_x$ is in a sterically hindered relationship relative to $CpS_y$ sufficient to prevent rotation of said rings and impart stereorigidity to said catalyst. In addition, the Cp rings substituents are positioned is such a manner as to impart to the metallocene compound a $C_2$ or $C_s$ symmetry.

Me is a Group IVB, VB or VIB 6 metal from the Periodic Table of Elements;

Q is a hydrocarbyl radical having from 1–20 carbon atoms or is a halogen.

x is from 1 to 5; y is from 1 to 5; k is from 0 to 3.

The stereorigid metallocene catalyst as characterized above may be neutral or cationic metallocene. The cationic metallocenes correspond to the structure depicted by formula (2) with the exception that k is an integer from 0 to 2 rather than the transition metal being possible tri-substituted as the case of the neutral metallocene. Cationic metallocene catalysts of the type in which stereorigidity is provided by means of direct steric hindrance, as in the case of the catalyst formula (2) above, may be characterized by formula (3) as follows:

In formula (3), S, S', x, y, Me and Q are the same as described previously with respect to formula (2). k is a number from 0–2 and P is a stable noncoordinating counter anion.

BRIEF DESCRIPTION OF THE DRAWINGS

A more complete appreciation of the invention and many of the attendant advantages thereof will be readily understood by reference to the following detailed description when considered in connection with the accompanying drawings.

DETAILED DESCRIPTION OF THE PREFERRED EMBODIMENT

Figure 1:
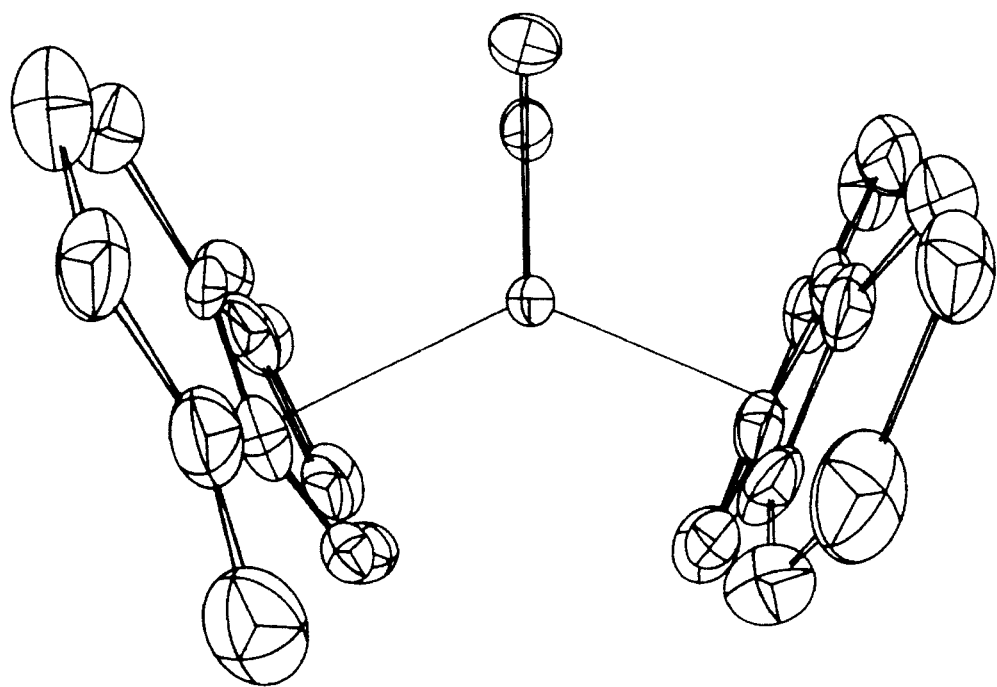
FIG. 1 is the crystal structure of bis(methylfluorenyl)zirconium dichloride (View 1, side view).
Figure 2:
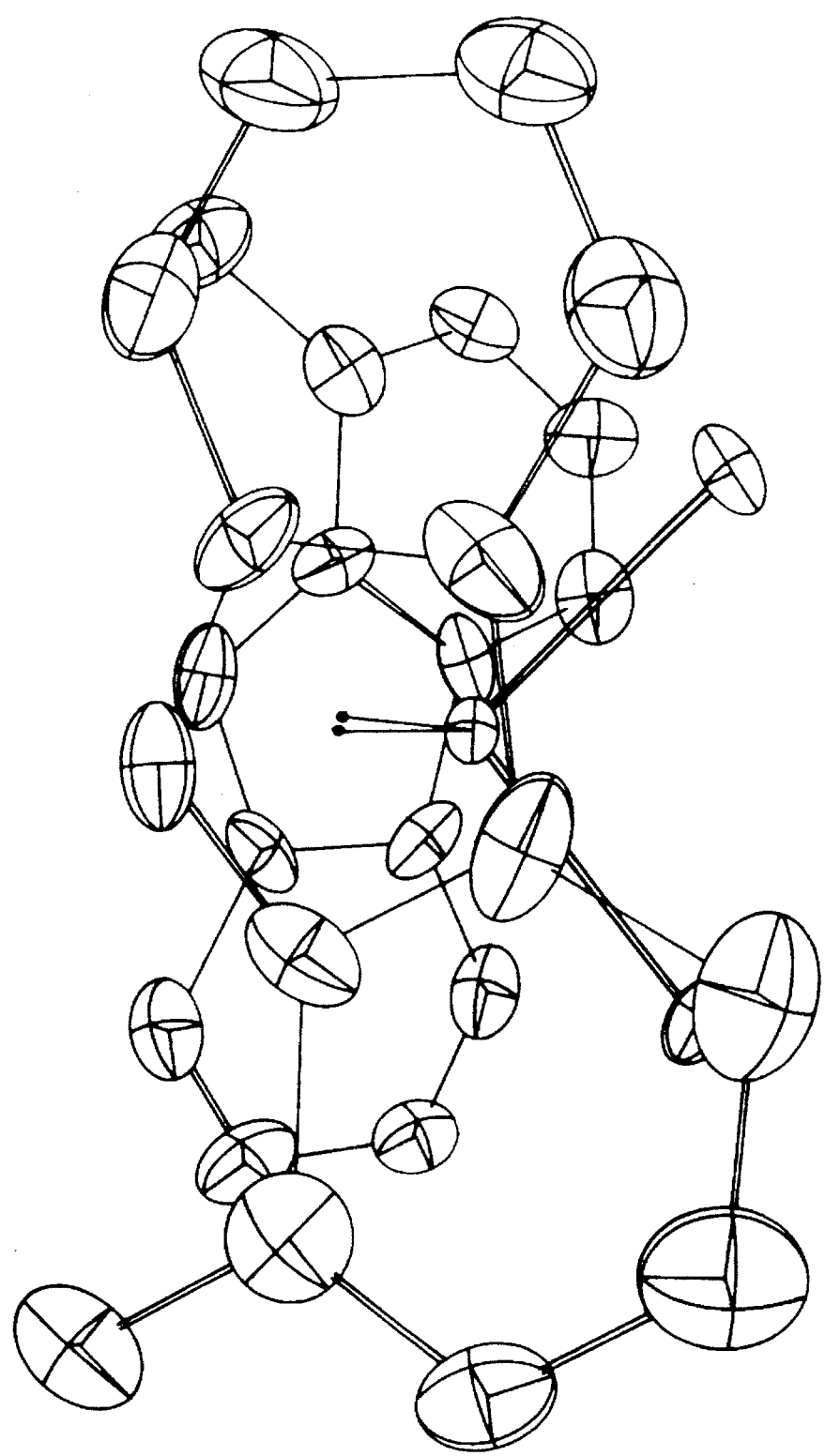
FIG. 2 is the crystal structure of bis(methylfluorenyl)zirconium dichloride (View 2, top view).
Figure 3:
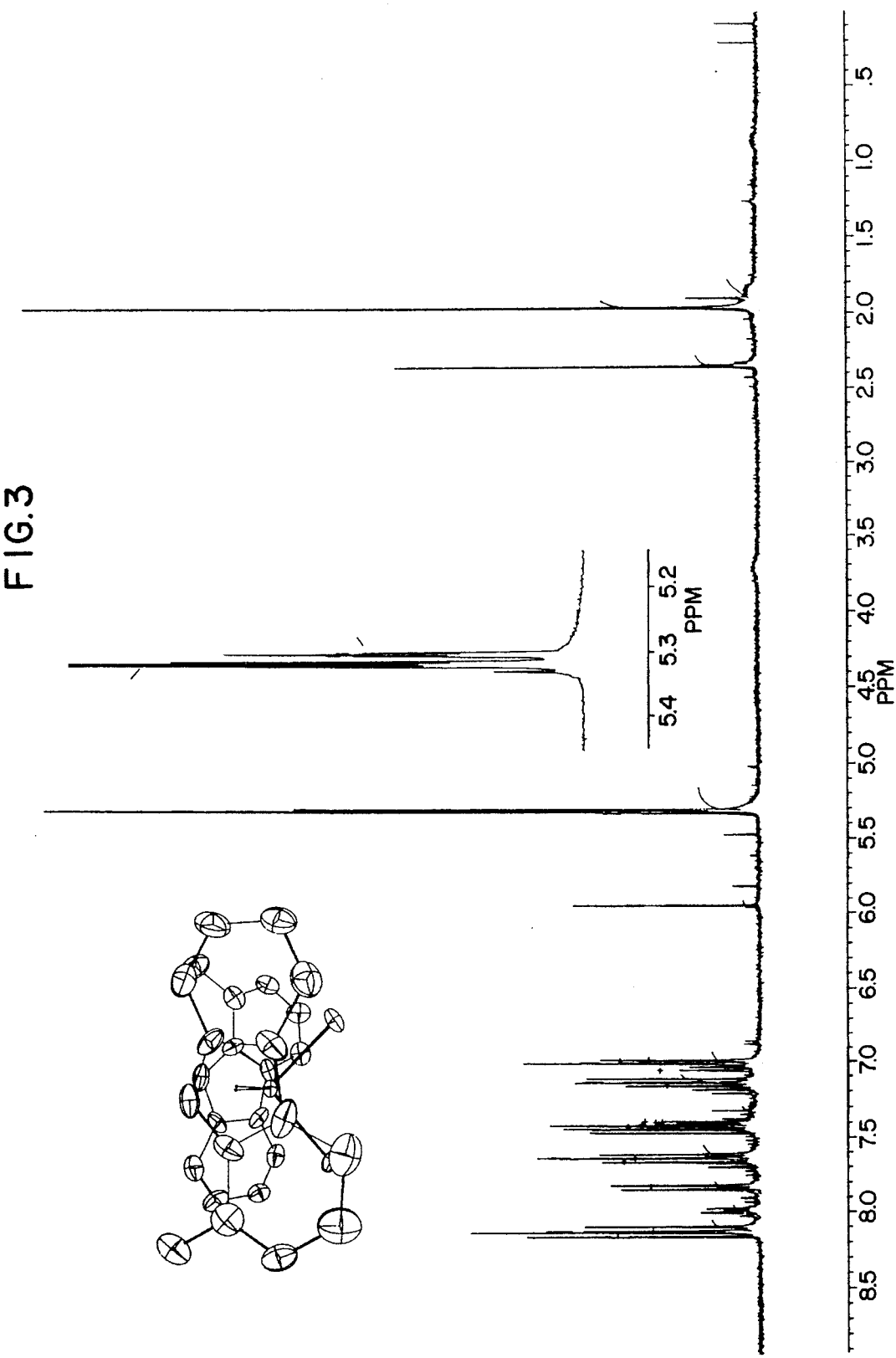
FIG. 3 is the $^1H$ NMR spectra of bis(methylfluorenyl)zirconium dichloride.
Figure 4:
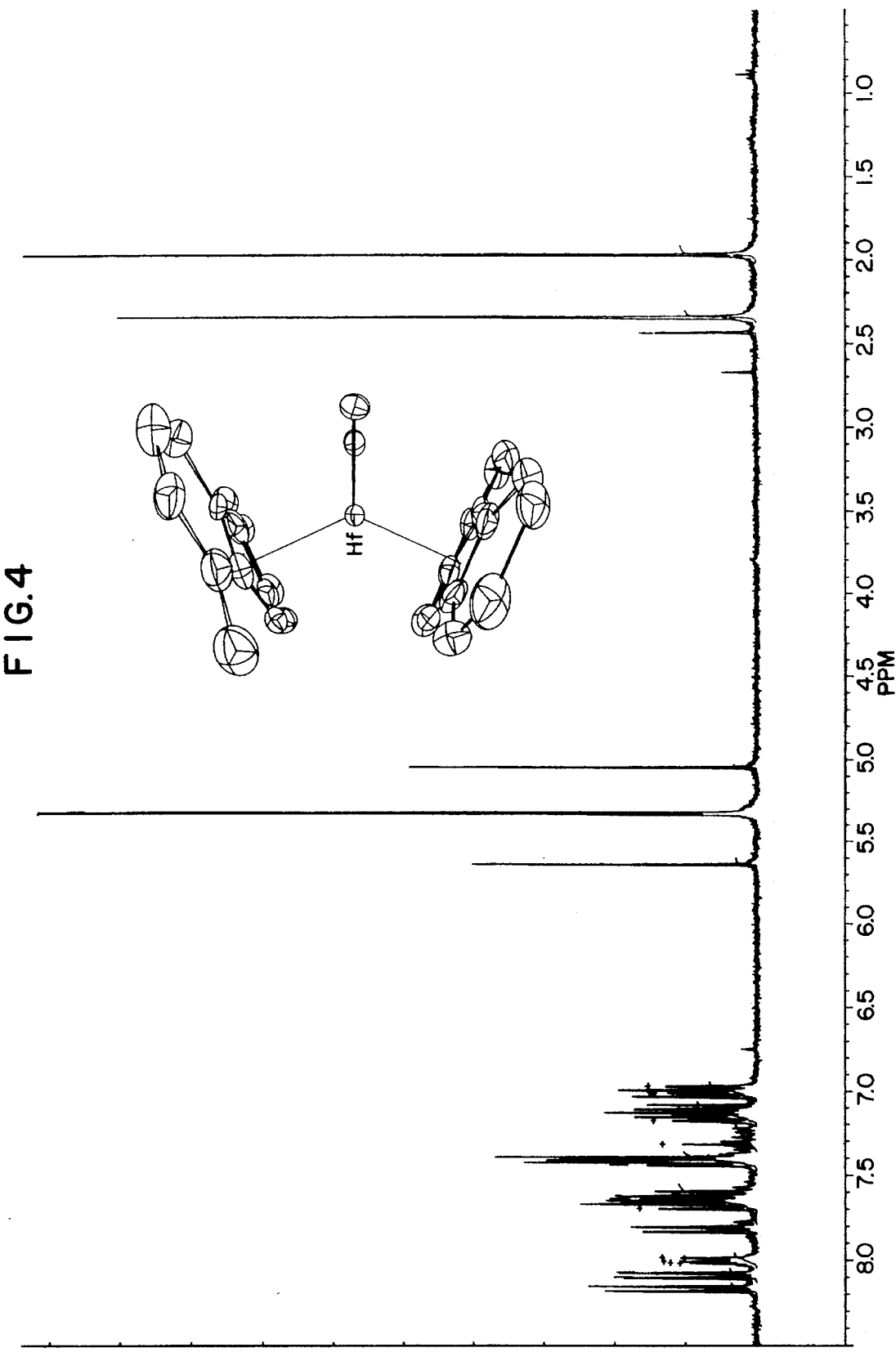
FIG. 4 is the $^1H$ NMR spectra of bis(methylfluorenyl)hafnium dichloride.
Figure 5:
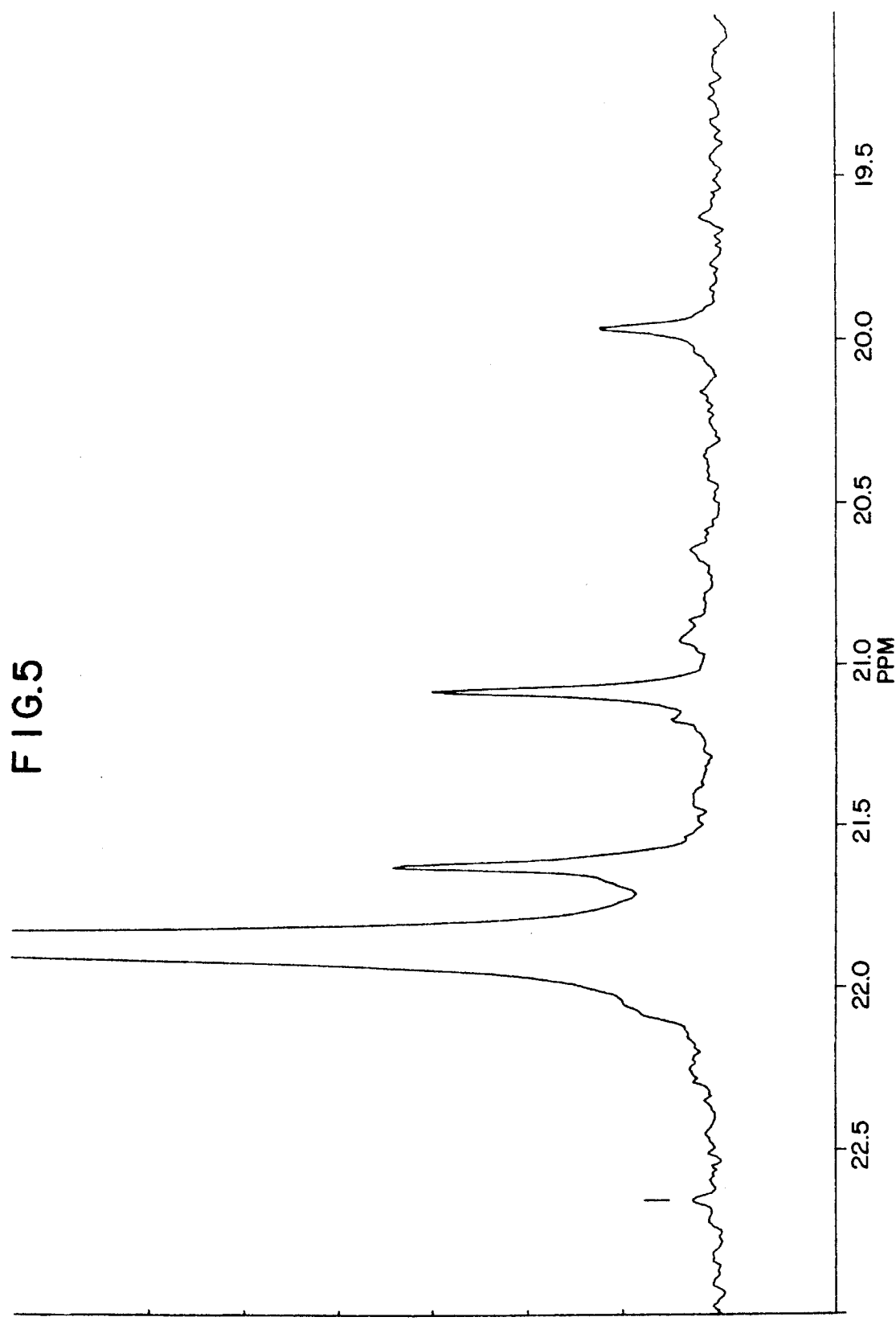
FIG. 5 is the $^{13}C$ NMR spectra of the polymer produced by bis(methyl fluorenyl)zirconium dichloride.
Figure 6:
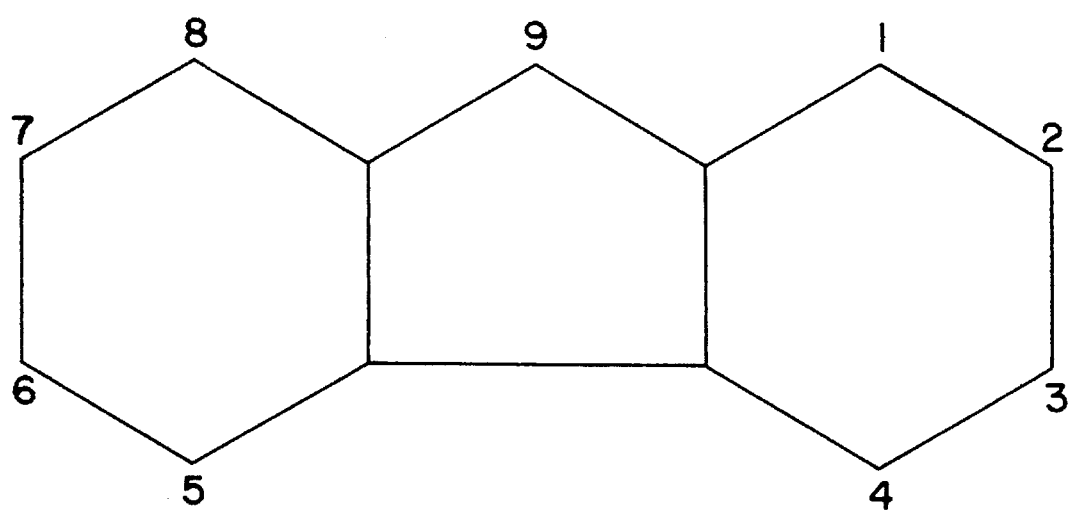
FIG. 6 shows the numbering system for any substituents present on the fluorenyl radical.

The present invention involves certain stereorigid metallocenes which may be neutral or cationic and their use as catalysts in stereospecific polymer propagation. The term metallocene as used herein and in accordance with normal art usage denotes an organometallic coordination compound in which two cyclo-$C_5$ ligands (cyclopentadienyl or substituted cyclopentadienyl rings) are bonded to a central or "sandwiched" metal atom which may be provided by a transition metal or metal halide, alkyl, alkoxy, or alkyl or alkoxy halide or the like. Such structures are sometimes referred to as "molecular sandwiches" since the cyclo-$C_5$ ligands are oriented above or below the plane of the central coordinated metal atom. By the term "cationic metallocene" is meant a metallocene in which the central coordinated metal atom carries a positive charge, that is, the metallocene complex is a cation associated with a stable anion. Both the neutral and the cationic metallocenes involved in the present invention are stereorigid. Stereorigidity is imparted to the metallocene complex to prevent rotation of the substituted cyclopentadienyl rings about their coordination axes by physical or structural relationships imparted by one or more of several ways. Stereorigidity may be imposed by means of substituted cyclopentadienyl rings in which the substituent groups provide for steric hindrance in the conventional sense of nonbonded spacial interaction between the two substituted cyclopentadienyl rings.

As noted previously, U.S. Pat. No. 4,892,851 discloses the preparation of syndiotactic polypropylene, or other polyolefins, through the use of stereorigid metallocene catalysts. The present invention employs stereorigid metallocene catalysts in which stereorigidity is imparted without a bridge structure and in which the metallocene ligand may be neutral or may be ionized to provide a stable cationic catalyst. The cationic metallocene catalysts employed in the present invention may be prepared following procedures of the type disclosed in the aforementioned European Publication Nos. 277 003 and 277 004, but they preferably are prepared by a process disclosed in European Patent Application Nos. 90870175.8 (published as Publication Nos. 0 426 637 A1 and 0 426 638 A2, respectively, both on May 8, 1991). In the metallocene catalysts disclosed in Publication Nos. 277 003 and 277 004, the cyclopentadienyl groups may be the same or different, and while they can be bridged, thus imparting stereorigidity they need not be and, in fact, are usually unbridged.

Stereorigid cationic metallocene catalysts employed in the present invention may be characterized by the following general formulas:

$$(CpX_x)(CpS'_y)MeQ_k \qquad (2)$$

wherein: Cp, S, S', Me, Q, k, x and y are as described previously. It will be recalled that k can be within the range of 0 to 2 for both neutral or cationic catalyst, and can be 3 for the neutral catalysts.

In the catalysts of formula (2), stereorigidity is imparted by means of direct steric hindrance between the two substituted cyclopentadienyl groups provided by relatively bulky or long chain substituents groups represented by S and S'. At the polymerization conditions, the two cyclopentadienyl groups are in a sterically hindered relationship sufficient to prevent rotation of the cyclopentadienyl rings, thus imparting stereorigidity to the catalyst. The steric relationships described above hold true for the cationic metallocenes characterized specifically characterized in formula (3) as well as for the neutral metallocenes of formula (2).

The counter anion indicated by P in formula (3) is a compatible noncoordinating anion which may be of the type described in the aforementioned Publication Nos. 277 003 and 277 004. The anion P either does not coordinate with the metallocene cation or is only weakly coordinated to the cation thereby remaining sufficiently labile to be displaced by a neutral Lewis base. As described in these applications, the term "compatible noncoordinating anion" identifies as anion which when functioning as a stabilizing anion in the metallocene catalyst system does not transfer an anionic substituent or fragment thereof to the cation to form a neutral metallocene and boron byproduct or other neutral metal or metalloid byproduct, as the case may be. Suitable noncoordinating anions include: $[W(PhF_5)]-, [Mo(PhF_5)-]$ (wherein $PhF_5$ is pentafluorenyl phenol) $[ClO_4]-, [PF_6]-,$ $[SbR_6]-, [AlR_4]-$ (wherein each R is independently, Cl, a $C_1-C_5$ alkyl group, preferably a methyl group, an aryl group, e.g., a phenyl or substituted phenyl group, or a fluorinated aryl group. For a further description of compatible noncoordinating anions and their associated cations which may be employed in the present invention, reference is made to European Publication Nos. 277 003 and 277 004, the entire disclosures of which are incorporated herein by reference. The size of the counter ion will depend on the bulk of the substituent groups on the cyclopentadienyl rings and the manner in which stereorigidity is imparted to the metallocene structure. Where bridged metallocene structures of the type disclosed in U.S. Pat. No. 4,892,851 are employed, the basic requirement for production of the syndiotactic polymers is that the cyclopentadienyl rings be dissimilar and, of course, at least one ring being substituted. With stereorigidity provided by the bridge structure, monomer insertion and isomerization is controlled primarily by the relationship of the anionic counterion to the bridged structure.

In the present invention, stereorigidity is imparted, as noted above, by means of direct steric hindrance imparted by the cyclopentadienyl substituent groups. Relatively more bulky substituent groups are required and steric relationships are developed not only between the cyclopentadienyl substituents but also between the substituents and the noncoordinating anion. Here, the size of the anionic counterion may be slightly smaller than the bridged structures where steric hindrance is not significant, or at least is not as significant, as in the nonbridged structure. In addition to size, the other important characteristics of the anionic counterions are stability and bonding. The anion must be sufficiently stable so that it cannot be rendered neutral by virtue of the metallocene cation extracting an anionic substituent or fragment. The bond strength with the cation is such that it must be noncoordinating or only weakly coordinating with the metallocene cation so that it makes way for the inserting monomer in the chain growing reaction.

The metallocene catalysts disclosed in the European Publication Nos. 277 003 and 277 004 suffer from certain disadvantages in that Lewis bases may be produced by protonation of the metallocene ligand which function as poisons for the metallocene catalyst. A preferred procedure for producing cationic metallocene catalyst of the type employed in the present invention involves the reaction of an anionic compound in a noncoordinating solvent with a neutral dimethyl metallocene of the type depicted by formula (2), i.e., where Q is $CH_3$ and k is 2. By way of example triphenylcarbenium tetrakis (pentafluorophenyl) boronate may be reacted with the neutral metallocene in a solvent such as toluene. Such catalysts and their preparation are disclosed in European Patent Application 90870174.1 (Publication No. 0 426 637 A2) for "Preparation of Metallocene Catalysts for Polymerization of Olefins", the entire disclosure of which is incorporated by reference.

A preferred application of the invention is in the syndictactic polymerization of $C_3+$ alpha olefins, specifically propylene, but the invention may be employed in the preparation of other polymers from ethylenically unsaturated monomers where syndiotacticity is a desired structure. By the terms ethylenically unsaturated monomer as used herein is meant a hydrocarbon or substituted hydrocarbon compound characterized by a terminal vinyl group ($CH_2=CH-$). Such compounds as may be employed in the present invention have at least three carbon atoms or are a substituted vinyl compound, specifically vinyl chloride. They may be characterized in terms of the following formula:

$$CH_2=CH-R \qquad (4)$$

wherein: R is a hydrocarbyl group or nonhydrocarbyl substituent. For example, syndicspecific propagation of a polymer chain from 1 butene may be carried out in accordance with the invention. Specific polymers in which stereospecificity is sometimes desirable and to which the invention is applicable include polyvinyl chloride and polystyrene. The polymerization of a 1-diene such as 1,3-butadiene may also be carried out in accordance with the present invention to achieve a stereospecific polymer configuration. Isotactic polypropylene is probably of the greatest practical significance and the invention will be described in detail with reference to the production of isotactic polypropylene. However, other compounds in which both the isospecific and syndiotactic configuration is desirable are also of interest.

Polymerization procedures as disclosed in the aforementioned U.S. Pat. No. 3,892,851, European Patent Publication No. 0 426 637 A2 and European Patent Publication No. 0 426 638 A2, hereby incorporated by reference, be employed in carrying out the present invention. However, aluminoxane which may be used as a co-catalyst in the U.S. Pat. No. 4,892,851 need not be, and preferably is not, used in carrying out the present invention where cationic catalysts of the type depicted by formula (3) are used. Where the catalyst used in carrying out the invention is a neutral metallocene, an aluminoxane should be used following the teachings of U.S. Pat. No. 4,892,851. Useful alumoxanes, either in the polymerization reaction or in forming the complex, may be characterized by the general formulas: $(R-Al-O-)$ in the cycle form and $R(R-Al-OO_n-AlR_2$ to the linear form wherein R is an alkyl group with one to five carbon atoms and n is an integer from 1 to about 20. Most preferably, R is a methyl group.

While applicants' invention is not to be restricted by theory, it is believed that neutral metallocenes form cationic complexes by reaction with the aluminoxanes in the manner as disclosed by Zambelli, A., et al., "Isotactic Polymerization of Propene" Homogeneous Catalysts Based on Group 4 Metallocenes Without Methylaluminoxane", Macro-Molecules 1989, 22, pages 2186–2189. It is believed that the anionic species derived from the aluminoxane compound may function to stabilize the cationic metallocene to permit chain migration and isomerization during the growth of the polymer chain resulting in syndiotacticity. The stereorigid cationic metallocene catalysts employed in the present invention accomplish isomerization during monomer insertion and chain migration.

The procedures and reaction conditions disclosed in the aforementioned U.S. Pat. No. 3,892,851 may be employed in the present invention when neutral metallocenes are used. Where the catalyst employed in the invention is a cationic metallocene, the procedure and reaction conditions disclosed in the aforementioned European Patent Application Publication Nos. 277 003, 277 004, 0 426 637 A2 and 0 426 638 A2 may be employed in the present invention. The prior art discloses the use of aluminoxanes as co-catalysts with metallocene catalysts in amounts well in excess of a stoichiometric equivalent amount providing mole ratios of aluminum to the coordinating metal (Me) of about 100–1000. Aluminoxanes usually are not employed in the present invention with cationic metallocenes and if they are used they are in amounts well below the aforementioned range and preferably providing an Al/Me mole rate of no more than 10 and, more preferably, no more than 1.

The catalysts used in the present invention are stereospecific and produce a polymer with a high tacticity.

The metallocene catalysts used in the present invention may be characterized by formulas (2) and (3) as described above. Me is a Group IVB, VB, or VIB metal from the Periodic Table of Elements but preferably is a Group IVB or VB metal and more preferably a Group IVB metal, specifically titanium, zirconium or hafnium. Vanadium is the most suitable of the Group VB metals. Each Q is a hydrocarbyl radical having 1–20 carbon atoms or is a halogen. As a practical matter, Q will usually be a methyl or ethyl group or a halide, preferably chlorine.

In the preferred catalysts for use in the present invention, Me is titanium, zirconium or hafnium; Q is a hydrocarbyl group, preferably methyl, or a halogen, preferably chlorine; and k is preferably 1 in the case of cationic Group IVB metallocenes and 2 in the case of neutral Group IVB metallocenes, but it may vary with the valence of the metal atom. Exemplary hydrocarbyl radicals in addition to methyl include ethyl, propyl, isopropyl, butyl, isobutyl, amyl, isoamyl, hexyl, heptyl, octyl, nonyl, decyl, cetyl, phenyl, and the like. Other hydrocarbyl radicals useful in the present catalysts include other alkyl, aryl, alkenyl, alkylaryl or arylalkyl radicals. Further $S_x$ and $S'_y$ may comprise hydrocarbyl radicals attached to a single carbon atom in the Cp ring as well as radicals that are bonded to two carbon atoms in the ring. The cationic catalysts used in the present invention may be derived from a neutral metallocene moiety prepared in accordance with any suitable procedures, such as described later herein, which is then converted to the cationic state, following procedures such as disclosed in the aforementioned European Publication Nos. 277 003 and 277 004, or more preferably, by following procedures such as disclosed in European Publication Nos. 0 426 637 A2 and 0 426 638 A2.

In the nonbridged metallocene catalysts of formula (2) or (3) stereorigidity is imparted by steric hindrance due to nonbonded interaction between the two substituted cyclopentadienyl rings. Stereorigidity is provided due to the fact that the substituent groups of the cyclopentadienyl rings interact in a spacial arrangement between rings such that rotation of the rings relative to the zirconium or other transition metal atom is prevented or at least retarded to a substantial extent. Examples of such metallocenes providing for direct steric hindrance include metallocenes of transition metals as described previously, preferably hafnium, zirconium or titanium, in which the metallocene ligand includes ring structures having two or more substituents with a total of at least five substituents on both cyclopentadienyl rings. Examples include (dialkylcyclopentadienyl) (trialkylcyclopentadienyl) and (trialkylcyclopentadienyl) (tetralkylcyclopentadienyl) groups. Other substituted cyclopentadienyl radical pairs forming the ligand include disubstituted, tetra substituted ring pairs, tri substituted, tetra substituted ring pairs, and di substituted penta substituted ring pairs. Suitable ligand structures include (1,2 dialkylcyclopentadienyl) (1,3,4 trialkylcyclopentadienyl), (1,3-dialkylcyclopentadienyl) (1,3,4 trialkylcyclopentadienyl), (1,2,3 trialkylcyclopentadienyl, (tetralkylcyclopentadienyl), (1,2 dialkylcyclopentadienyl) (tetralkyicyclopentadienyl), (1,2,4 trialkylcyclopentadienyl), (tetralkylcyclopentadienyl), (1,3-dialkylcyclopentadienyl) (1,2,3,4tetralkylcyclopentadienyl), (1,3 dialkylcyclopentadienyl) (pentalkylcyclopentadienyl. Suitable ligand structures to produce isotactic polyolefins include 1 -alkyl fluorenyl, 2-alkyl fluorenyl, 3-alkyl fluorenyl and 4-alkyl fluorenyl or any other arrangement of the substituents imparting the property of $C_2$ or pseudo-$C_2$ symmetry to the final metallocene compound. Suitable ligand structures to produce syndiotactic polyolefins include 2,7-dialkyl fluorenyl, 3,6-dialkyl fluorenyl, 4,5-dialkyl fluorenyl, 1,8-dialkyl fluorenyl, 1,2-dialkyl-3,4-dialkyl fluorenyl, 2,3-dialkyl-6,7-dialkyl fluorenyl, 3,4-dialkyl-5,6-dialkyl fluorenyl or any other arrangement of the substituents imparting the property of $C_s$ or pseudo-$C_s$ symmetry to the final metallocene compound. The terms "$C_2$ symmetry" and "$C_s$ symmetry" are used as defined in "advanced Inorganic Chemistry; Cotton and Wilkinson, $4^{th}$ ed, pages 28–60, hereby incorporated by reference.

The corresponding alkylsilyl substituted cyclopentadienyl groups may also be used in forming the metallocene ligand.

Specific substituent groups which may be employed in providing direct steric hindrance of the metallocene catalyst include: $CH_3$—, $C_2H_5$—, $C_3H_7$—, $(CH_3)_3C$—, $(CH_3)_3CH_2$—, $(CH_3)_3Si$—, $(C_2H_5)_3C$—$(C_2H_5)_3C\ CH_2$—, $(C_2H_5)_3Si$—. Further specific examples of sterically hindered ligand structures include (1,3 dipropylcyclopentadienyl))1,2,4 triethylcyclopentadienyl), and (1,2 diisobutylcyclopentadienyl) (triethylcyclopentadienyl).

In synthesizing the nonbridged metallocene catalysts of the present invention, any suitable technique can be used to produce substituted cyclopentadienyl groups which may be lithiated, for example, following a protocol such as disclosed in U.S. Pat. No. 4,892,851 for reaction with a transition metal chloride to form the neutral metallocene ligands of the present invention. However, in formulating the neutral metallocenes as end products or as precursors for later conversion to cationic metallocene of the present invention, the lithiated substituted cyclopentadienyl groups are reacted stepwise with the transition metal salt, e.g., zirconium or titanium tetrachloride, with the product of this reaction reacted with the other dissimilar bulky substituted cyclopentadienyl group. By way of example using the conventions Cp' and C' to designated dissimilar cyclopentadienyl groups having bulky and/or sterically hindered substituents as described above, a lithiated Cp' group may be reacted with zirconium tetrachloride to produce the dicyclopentadienyl (Cp$_2$) zirconium dichloride. The resulting product may be chlorinated to produce the monocyclopentadienyl zirconium trichloride and this product (Cp'ZrCl$_3$) then reacted with the lithiated Cp" group to produce the product (Cp'), (Cp") ZrCl$_2$. Those skilled in the art will recognize that this stepwise reaction formate can be followed to produce metallocene based upon titanium, zirconlure, hafnium, vanadium or other suitable transition metals.

Bulky substituted cyclopentadienyl groups from which metallocene ligands are formed can be derived by any suitable technique. Starting materials include benzyl alcohol, ketones of substituted cyclopentadienes, e.g., tetraphenylcyclopentadiene-1-ketone and substituted fulvenes. By way of example, pentabenzylcyclopentadiene can be produced by reaction of 5 moles of benzyl alcohol with 1 mole of cyclopentadiene in the presence of particulate sodium. The sodium acts to promote ring aromatization as is well known in the art. Pentaphenylcyclopentadiene can be produced by reaction of tetraphenylcyclopentadienyl-1-ketone) with phenyl lithium. This same reaction route can be used to produce other penta-substituted cyclopentadienes. For example, substituted cyclopentadienyl-1-ketone can be reacted with an alkyl lithium such as methyl, lithium, ethyl lithium, n-propyl or isopropyl lithium, or normal butyl or tertiary butyl lithium in tetrahydrofuran to form the corresponding penta-substituted cyclopentadiene, for example methyl tetraphenylcyclopentadiene and the corresponding ethyl, propyl, isopropyl, butyl, and tertiarybutyl tetraphenylcyciopentadienes. Benzyl tetraphenylcyclpentadiene and pentaphenylcyclopentadiene can also be prepared by this reaction route using phenyl lithium and beryl lithium, respectively.

The reaction of methyl lithium or another alkyl lithium with a tetra substituted dimethylfulvene may be employed to arrive at the bulky substituted cyclopentadienyl groups. For example, tetraphenyl-6-dimethylfulvene may be reacted with methyl lithium or ethyl lithium to produce tert-butyl cyclopentadiene. The resulting substituted cyclopentadienes can be reacted through the previously described stepwise procedure with a transition metal halide, e.g., titanium hafnium or zirconium tetrachloride, to produce the corresponding dichloride in which dissimilar substituted cyclopentadienyl groups are coordinated with the titanium, zirconium or other transition metal in the neutral metallocene complex. It will be recognized from the foregoing that numerous metallocene ligands having dissimilar bulky substituted cyclopentadienyl groups can be prepared following the reaction formats indicated above. In addition to those described previously, such ligands include (pentabenzylcyclopentadienyl) (ethyl tetraphenylcyclopentadienyl), (pentabenzylcyclopentadienyl), (propyltetraphenylcyclopentadienyl), (benzyltetraphenyl cyclopentadienyl) (tetrabenzyl cyclopentaclienyl) and (isoamyltetraphenylcyclopentadienyl) (methyltetraphenylcyclopentadienyl).

Sterically hindered metallocenes with more linear substituent groups to impart stereorigidity can be produced following protocols similar to those above. An alternative approach is through the formation of substituted cyclopentenones by cyclization or ring closure reactions involving substituted olefinic carboxylic acids or esters. The cyclization reaction can be carried out in accordance with any suitable procedure to produce the corresponding cyclopentenone. The substituted cyclopentenone may be reduced to an alcohol by any of the well known reduction reactions for conversion of cyclic ketones to the corresponding alcohols. For example, lithium or sodium aluminum hydride can be employed to reduce the substituted cyclopentenone to the corresponding substituted cyclopentenol. A dehydrating agent such as sulfuric acid or oxalic acid can then be used to dehydrate the substituted cyclopentenol to the corresponding substituted cyclopentadiene. The reaction of polyphosphoric acid on substituted alpha-ethylenic esters can be used for the preparation of substituted cyclopentadienes used in formulating sterically hindered metallocenes. Examples include reactions of polyphosphoric acid on substituted acrylates or crotonates. For examples, methyl-2-n-butyl crotonate, isopropyl crotonate, or butyl crotonate can be reacted with polyphosphoric acid to produce the corresponding substituted cyclopentenones. These reactions can take place at temperatures in the range of 60°–100° C. with the reaction times varying from a few minutes to a few hours. The resulting ketones are reduced by $LiAlH_4$ to the corresponding alcohols and the alcohols then dehydrated to yield the desired substituted cyclopentadienes. These, in turn, can be aromatized and reacted with the appropriate transition metal halide, for example titanium, hafnium or zirconlure tetrachloride to produce the metallocenes. Similar reactions with polyphosphoric acid can be carried using acrylic esters, e.g., methylacrylate. The resulting substituted cyclopentadienes can be reacted through the previously described stepwise procedure with a transition metal halide, e.g., titanium hafnium or zirconium tetrachloride to produce the corresponding dichloride in which dissimilar substituted cyclopentadienyl groups are coordinated with the titanium, zirconlure or other transition metal in the neutral metallocene complex. It will be recognized from the foregoing that numerous metallocene ligands having dissimilar bulky substituted cyclopentadienyl groups can be prepared following the reaction formats indicated above. In addition to those described previously, such ligands include (pentabenzylcyclopentadienyl) (ethyl tetraphenylcyclopentadienyl), (pentabenzylcyclopentadienyl), (propyltetraphenylcyclopentadienyl), (benzyltetraphenyl cyclopentadienyl) (tetrabenzylcyclopentadienyl) and (isoamyltetraphenylcyclopentadienyl) (methyltetraphenylcyclopentadienyl).

The neutral metallocenes can be converted to the cationic state by any suitable technique. Preferably, such conversion is affected using a trityl compound such as triphenylcarbenium tetrakis (pentafluorophenyl borate) as described above. Other suitable techniques are disclosed in the aforementioned European Publication Nos. 277 003 and 277 004.

As noted previously, the nonbridged metallocene catalysts of formulas (2) and (3) are stabilized by employing them under low temperature polymerization conditions. For example, polymerization of propylene may be carried out at temperatures of down to about −78° C. or lower using the sterically hindered nonbridged metallocenes of the present invention. The temperatures at which the metallocene catalysts of the present invention are stereorigid can be determined for an individual catalyst based upon nuclear magnetic residence studies as described below. As a practical matter, the substituted cyclopentadienyl groups are at sufficiently low kinetic energy states induced by the substituent group so as to prevent rotation of the rings about their coordination axes at temperatures of less than −20° C. Much lower temperatures may be used, and as indicated previously, the polymerization of propylene can be carried out at temperatures of −78° C. or lower.

The temperatures at which a bulky substituted metallocene catalyst of the present invention becomes stereorigid can be readily determined through nuclear magnetic resonance studies as the temperature of the catalyst is lowered from room temperature condition. As the temperature is lowered associated, the peaks with the sterically different bulky substituted cyclopentadienyl groups will change in characteristics, typically broadening, and measurements can be taken at progressively decreasing temperature values until it is observed that no change in the NMR spectrum occurs when going from one temperature to the next. At this temperature, the metallocene ligand is in a stereorigid condition in which the substituted cyclopentadienyl groups are no longer rotating.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE I

Preparation of the bis(1-methylfluorenyl)ZrCl$_2$. 5g of 1-methylfluorenyl were dissolved in 150 ml of THF and aromatized with an equimolar amount of methyl lithium in ether at room temperature. After stirring the reaction mixture for two hours the solvents were evaporated and a red powder was obtained. This was suspended in 20 ml of pentane and reacted with 3.15 g of ZrCl$_4$. After three hours of stirring the red suspension was filtered and extracted with dichloro methane. Red crystals were obtained upon cooling to −20° C.

EXAMPLE III

Polymerization. The polymerization runs were performed in a predried and degassed 3-1 autoclave equipped with a paddle, an external water jacket for temperature control. A typical run consisted of the introduction of 5 mg of catalyst prepared in example 1 mixed with a wt 10% MAO solution in toluene under propylene pressure. After one liter of propylene was introduced into the reactor the temperature was raised to 60° C. The polymerization was continued for 60 minutes at a pressure of 30 bars. It was terminated by venting the reactor and cooling the system. 12 g of IPP were recovered. The results are shown in Table I.

EXAMPLE IV

The polymerization was carried out in the same way as in example III but at 40° C. for 60 minutes yielding 10 g of IPP polymer. The results are shown in Table I.

EXAMPLE V

The polymerization was performed in a 2–1 Buchi reactor with 6.52 mg of the catalyst of Example I and 15 ml of a 10 wt % MAO solution in toluene at 60° C. and for 15 minutes at pressure of 22 bar. 3 g of IPP were obtained. The results are shown in Table I.

EXAMPLE VI

The same way as in Example V but with 9.6 mg of catalyst and 15 ml of MAO with a polymerization time of 60 minutes. 10 g of IPP polymer was obtained. The results are shown in Table I.

EXAMPLE VII

As in Example VI but with 9.4 mg of the catalyst obtained in example II. 1 g of IPP polymer was obtained. The results are shown in Table I.

EXAMPLE VIII

The same procedure as in Example VII but at a polymerization temperature of 70° C. The results are shown in Table I.

TABLE 1

Polymerization conditions and results for the Bis(methylfluorenyl)MCl$_2$/MAO catalyst system; M = Zr, Hf

| Example | Catalyst Amount (Metal/mg) | MAO (ml) | Pol. Temp (°C.) | Pol. Time (min.) | Yield (g) | Mw[1] (× 1000) | $M_p$ % | mmmm[2] % | II[3] % m |
|---|---|---|---|---|---|---|---|---|---|
| 3 | Zr 5 | 10 | 60 | 60 | 12 | 82 | 138.9 | 69.72 | 88.22 |
| 4 | Zr 5 | 10 | 40 | 60 | 10 | 132 | 138.5 | 71.50 | 90.40 |
| 5 | Zr 6.52 | 15 | 60 | 15 | 3.0 | 37 | 139 | 81.56 | 89 |
| 6 | Zr 9.6 | 15 | 60 | 60 | 10 | 39 | 132 | nd | nd |
| 7 | Zr 9.35 | 15 | 70 | 60 | 1.0 | 13 | 117 | md | nd |
| 8 | Zr 9.4 | 15 | 60 | 60 | 1.5 | 12 | 120 | 50 | 66.5 |

[1]The Mw's in runs 3–6 are correct for purified hexane extracted portion of the polymer.
[2]The pentad (mmmm) given in the table is based only on stereoregular portion of the polymer after it was freed from the concomitant atactic portion by hexane extraction.
[3]The II of isotacticity index is equal the percentage of the meso dyad calculated from meso triads and pentads using Bovey's equation.

EXAMPLE II

Preparation of the bis(1-methylfluorenyl)HfCl$_2$. The procedure described in Example I was repeated with HfCl$_4$ being used instead of ZrCl$_4$.

Having described specific embodiments of the present invention, it will be understood that modification thereof may be suggested to those skilled in the art, and it is intended to cover all such modifications as fall within the scope of the appended claims.

What is claimed as new and desired to be secured by letter of patent of the United States of America is:

1. A process for the stereospecific propagation of a polymer chain derived form an ethylenically unsaturated monomer comprising:

(a) providing a catalyst comprising 1) a stereorigid neutral metallocene characterized by a metallocene ligand having ring structures joined to a coordinated transition metal atom, each of said ring structures being a substituted cyclopentadienyl ring and each of said ring structures being in a stereorigid relationship relative to said coordinating metal atom to prevent rotation of said rings structure, said stereorigid relationship being imparted by substituent groups on said ring structures and characterized by the formula:

$$(CpS_x)(CpS'_y)MeQ_k$$

wherein Cp is a cyclopentadienyl ring, S is a hydrocarbyl radical having from 1–20 carbon atoms, being the same or different, S' is a hydrocarbyl radical having from 1–20 carbon atoms, being the same or different, Me is a Group IVB, VB or VIB metal from the Periodic Table of Elements, Q is a hydrocarbyl having from 1–20 carbon atoms or is a halogen, x is from 1 to 5, y is from 1 to 5, k is from 0 to 3 and 2) an aluminoxane of the formula (R-Al-O-) in the cyclic form and $R(R-Al-O-)_nALR_2$ in the linear form wherein R is an alkyl group with one to five carbon atoms and n is an integer from 1 to about 20, (b) contacting said catalyst in a polymerization reaction zone with an ethylenically unsaturated monomer which contains 3 or more carbon atoms or which is a substituted vinyl compound and maintaining said reaction zone under polymerization conditions to produce crystalline polymer of said monomer.

2. The process of claim 1, wherein the transition metal of said catalyst is a Group IVB or Group VB metal from the Periodic Table of Elements.

3. The process of claim 2, wherein the transition metal of said catalyst is titanium, zirconlure or hafnium.

4. The method of claim 1, wherein said ethylenically unsaturated monomer is $C_{3+}$ hydrocarbon.

5. The method of claim 4, wherein said ethylenically unsaturated monomer is a vinyl aromatic compound.

6. The method of claim 5, wherein said vinyl aromatic compound is styrene.

7. The method of claim 1, wherein said ethylenically unsaturated monomer is a substituted vinyl compound.

8. The method of claim 7, wherein said substituted vinyl compound is vinyl chloride.

9. The method of claim 1, wherein said ethylenically unsaturated monomer is a $C_3+$ alpha olefin.

10. The method of claim 9, wherein said $C_3+$ alpha olefin is propylene.

11. The process of claim 1 wherein the metallocene is bis(1-methylfluorenyl)zirconium dichloride or bis(1-methyl fluorenyl)hafnium dichloride and the aluminoxane is methylalumoxane.

12. The catalyst of claim 1 wherein the aluminoxane is methylalumoxane.

13. The catalyst of claim 12 wherein the mole ratio of aluminum to the coordinating transition metal is about 100–1000.

14. A process for the stereospecific propagation of a polymer chain derived form an ethylenically unsaturated monomer comprising:

(a) providing a catalyst comprising 1) a stereorigid metallocene cation characterized by a metallocene ligand having ring structures joined to a coordinated transition metal atom, each of said ring structures being a substituted cyclopentadienyl ring and each of said ring structures being in a stereorigid relationship relative to said coordinating metal atom to prevent rotation of said rings structure, said stereorigid relationship being imparted by substituent groups on said ring structures and 2) a stable noncoordinating counter anion characterized by the formula:

$$[(CpS_x)(CpS'_y)MeQ_k]^+P^-$$

wherein Cp is a cyclopentadienyl ring, S is a hydrocarbyl radical having from 1–20 carbon atoms, being the same or different, S' is a hydrocarbyl radical having from 1–20 carbon atoms, being the same or different, Me is a Group IVB, VB or VIB metal from the Periodic Table of Elements, Q is a hydrocarbyl having from 1–20 carbon atoms or is a halogen, P is a stable noncoordinated counter anion, x is from 1 to 5, y is from 1 to 5, k is from 0 to 2, (b) contacting said catalyst in a polymerization reaction zone with an ethylenically unsaturated monomer which contains 3 or more carbon atoms or which is a substituted vinyl compound and maintaining said reaction zone under polymerization conditions to produce crystalline polymer of said monomer.

15. The process of claim 14 wherein Me is titanium, zirconium or hafnium and k is 1 or 2.

16. The process of claim 15 wherein each Q is a halogen or a methyl or ethyl group.

17. The process of claim 15 wherein Me is zirconium and k is 1.

18. The process of claim 17, wherein Q is a halogen or a methyl or ethyl group.

19. The process of claim 17, wherein Q is a chlorine or methyl group.

20. The catalyst of claim 14 wherein P is $[W(PhF_5)]^-$, $[Mo(PhF_5)]^-$, $[ClO_4]^-$, $[PhF_6]^-$, $SbR_6]^-$, $[AlR_4]^-$, wherein $PhF_5$ is pentafluorenyl phenol and R is independently $C_1$, a $C_1$–$C_5$ alkyl group, an aryl group, or a fluorinated aryl group.

* * * * *